United States Patent [19]
Cohen et al.

[11] Patent Number: 5,560,917
[45] Date of Patent: Oct. 1, 1996

[54] COSMETIC MAKEUP COMPOSITION

[75] Inventors: Kenneth A. Cohen; Harold Suss, both of Germantown, Tenn.

[73] Assignee: Maybelline Intermediate Company, Memphis, Tenn.

[21] Appl. No.: 382,396

[22] Filed: Feb. 1, 1995

[51] Int. Cl.$^6$ .................................................... A61K 6/00
[52] U.S. Cl. ........................... 424/401; 424/59; 424/63; 514/845; 514/847
[58] Field of Search ............................ 424/401, 63, 59; 514/845, 847

[56] References Cited

U.S. PATENT DOCUMENTS

| | | | |
|---|---|---|---|
| 4,970,220 | 11/1990 | Chaussee | 514/358 |
| 5,023,235 | 6/1991 | N'Guyen et al. | 424/401 |
| 5,032,390 | 7/1991 | Iwaya et al. | 424/59 |
| 5,093,109 | 3/1992 | Mausner | 424/63 |
| 5,114,716 | 5/1992 | N'Guyen et al. | 424/401 |
| 5,198,210 | 3/1993 | Critchley et al. | 424/78.03 |
| 5,204,105 | 4/1993 | Mausner | 424/401 |
| 5,254,331 | 10/1993 | Mausner | 424/59 |
| 5,294,444 | 3/1994 | Nakamura et al. | 424/401 |
| 5,368,857 | 11/1994 | Corcoran et al. | 424/401 |
| 5,393,526 | 2/1995 | Castro | 424/401 |
| 5,411,742 | 5/1995 | Sebag et al. | 424/401 |
| 5,486,352 | 1/1996 | Guerrero | 424/59 |

*Primary Examiner*—Mark D. Sweet
*Attorney, Agent, or Firm*—Sherman and Shalloway

[57] ABSTRACT

A water-in-oil emulsified cosmetic makeup composition includes sunscreen agent, free radical scavenger, moisturizing agent/re-hydrating agent, skin firming agent and cosmetically acceptable pigment. The composition when applied to the skin smoothes, moisturizes, firms and protects the skin from the effects of the environment and improves complexion.

16 Claims, No Drawings

COSMETIC MAKEUP COMPOSITION

BACKGROUND OF THE INVENTION

1. Field of the Invention

The present invention relates to a makeup composition and method for treating skin, and more particularly, to an improved pigmented makeup composition which, when applied topically to exposed skin, provides effective protection from the sun, moisturizes and soothes the skin, as well as provides an attractive coloration thereto.

2. Description Of the Prior Art

Aging, environmental conditions, such as heating and air conditioning, exposure to the sun and environmental pollution exert negative effects on human skin and result in wrinkles, sagging, loss of elasticity and firmness, dryness, changes in complexion and other cosmetically undesirable effects. A number of skin cream compositions exist that contain ingredients to counteract some of the effects of stress on the skin.

Sunscreens provide protection from sun-induced skin damage that accelerates skin aging. A number of patents relate generally to "anti-aging" cosmetic compositions that include a broad range of ingredients. These include, for example, free radical activity retarding compounds, titanium dioxide as sunscreen, antioxidants, emulsifiers, thickeners and colorants (e.g. U.S. Pat. No. 5,093,109); plant and yeast extracts, vitamin E or C for elasticity, silicone for firmness and sunscreens (e.g. U.S. Pat. No. 5,204,105); serum protein complex with hydrolyzed animal protein, protein-aminoacid-vitamin-nucleotide complex, dimethylsilanoyl hyaluronate complex and small micellar complexes containing various ingredients, such as for example panthenol (e.g. U.S. Pat. No. 5,254,331). Many cosmetic compositions and skin protective compositions contain titanium dioxide, alone, or mixed or treated with a silicone compound (U.S. Pat. No. 4,801,445) or titanium dioxide coated with or mixed with mica and/or silicone (U.S. Pat. No. 4,820,508) or microfine particles of titanium oxide (U.S. Pat. Nos. 5,032,390 and 5,250,289).

Sunscreens, however, are not effective against the natural formation of free radicals in the skin or against the natural breakdown of the water barrier of the skin caused by aging, which results in sagging and wrinkles. Compositions that include free radical activity retarding compounds are known (e.g. U.S. Pat. No. 5,093,109), however, these compositions are water based and contain non-stabilized free radical components, such as ascorbyl palmitate, which rapidly degenerates in an emulsion. Cosmetic topical compositions containing pseudoceramides to firm the skin are known (U.S. Pat. No. 5,198,210, U.S. Pat. No. 5,206,020 and U.S. Pat. No. 5,326,565), however, these compositions do not contain free radical scavengers and/or sunscreens.

Accordingly, there is a need for a single cosmetic makeup that is effective in retarding the effects of sunlight, retarding the effects of aging on the skin, such as drying and loss of firmness and elasticity, while providing an attractive coloration to improve the complexion of the skin.

SUMMARY OF THE INVENTION

The present invention provides an emulsified cosmetic makeup composition for smoothing, moisturizing, firming, and protecting human skin from the effects of sunlight, and improving the complexion of the skin. The composition comprises, consists essentially of, or consists of a water-in-oil emulsion in which there is emulsified and dispersed, in cosmetically acceptable and effective amounts (a) sunscreen agent;

(b) free-radical scavenger;

(c) moisturizing agent/re-hydrating agent;

(d) skin firming agent; and (e) cosmetically acceptable pigment.

A particularly preferred emulsified cosmetic makeup composition for smoothing, moisturizing, firming and protecting human skin from the effects of sunlight and improving the complexion of the skin includes in a water-in-oil emulsified base, based on the total weight of the composition, from about 0.1 to 20 wt % silicone-treated, aluminum oxide coated ultrafine titanium dioxide particles; from about 0.1 to 2% free-radical scavenger; from about 0.5 to 13% of a blend of moisturizers and rehydrating agents including evening primrose oil; from about 0.0001 to 0.1% of a mixture of animal and/or botanical ceramides and glycolipids; and from about 0.5 to 25% of a blend of cosmetically acceptable pigments, particularly dimethicone-coated inorganic pigments.

In another aspect of the invention there is provided a method of smoothing, firming, moisturizing, protecting from sunlight and improving the complexion of human skin. The method involves topically applying to the skin a cosmetically effective amount of a water-in-oil emulsified makeup composition the essential ingredients of which include, in cosmetically effective amounts, skin firming agent, particularly a mixture of ceramides and glycolipids; sunscreen agent; moisturizing agent/rehydrating agent, cosmetically acceptable pigment and free-radical scavenger.

DETAILED DESCRIPTION AND PREFERRED EMBODIMENTS

The present invention provides a cosmetic makeup composition in a pigmented emulsified base suitable for treatment of the skin. The present makeup composition is a water-in-oil emulsion containing "anti-aging" components, e.g. free radical scavenger(s), sunscreen(s), moisturizing/rehydrating component(s), and optionally an antioxidant component as a free radical scavenger antioxidant. The present emulsified cosmetic makeup composition is effective against sun-induced aging and natural aging. When applied to the skin, the present composition retards the effects of aging caused by exposure of the skin to sunlight and natural aging, moisturizes and re-hydrates dry skin and provides an attractive coloration to the skin. This composition is advantageous because it combines the effects of pigmented makeups, moisturizers, re-hydrating agents, sunscreens and bioactive agents, such as vitamins and extracts of plants, which retain their biological activities, in a single, easy to apply, composition.

The anti-aging skin cream makeup composition of the present invention contains a water-in-oil emulsion having dispersed therein the following essential active ingredients:

(1) sunscreen agent;

(2) free radical scavenger;

(3) moisturizing agent/re-hydrating agent;

(4) skin-firming agent, and (5) cosmetically acceptable pigment, each present in a cosmetically effective amount. Optionally, the makeup composition of this invention also contains at least one of anti-irritant agent, calming and/or soothing agent. Preferred embodiments of the invention include as sunscreen agent dimethicone-treated ultrafine particles of titanium dioxide coated with aluminum oxide; as free-radical scavenger stabilized vitamin E, stabilized vitamin C, Ginkgo biloba or a combination thereof; and as skin firming agent a mixture of animal and/or botanical ceramides and glycolipids. Broad and preferred ranges of ingredients and other optional ingredients in the makeup composition are presented in Table 1. It will be recognized that some of the ingredients of the composition have dual functions due to the nature of their chemical structure and activities. For example, emollients such as shea butter also function as sun protection factor (SPF) boosters; moisturizers, such as vitamin E acetate also function as antioxidants; and propylene glycol functions as both a preservative and humectant.

TABLE 1

| Ingredient | % by weight of total composition | |
|---|---|---|
| | Broad | Preferred |
| AQUEOUS SOLVENT | 20–75 | 30–45 |
| OIL CARRIER FLUID | 5–50 | 10–25 |
| SUNSCREEN AGENT | 0.1–20 | 6–10 |
| FREE-RADICAL SCAVENGER | 0.1–2 | 0.15–1 |
| MOISTURIZER/REHYDRATING AGENT | 0.5–13 | 1–10 |
| SKIN FIRMING AGENT | 0.0001–0.1 | 0.01–0.05 |
| PIGMENT/COLORANT | 0.5–25 | 5–15 |
| OPTIONAL INGREDIENTS/ADJUVANTS | | |
| Anti-Irritant/Healing Agent | 0.01–5 | 0.25–2.5 |
| Emollient | 0.5–25 | 5–15 |
| Antioxidant (Free radical scavenger activity) | 0.01–5 | 0.25–1 |
| Preservative | 0.1–1.5 | 0.25–0.75 |
| Humectant | 0.5–25 | 1–5 |
| Emulsifier | 0.5–6.0 | 2–3.5 |
| Filler | 0.01–10.0 | 0.05–5 |
| Fragrance | 0.1–1.0 | 0.15–0.35 |
| Wax | 0.1–0.5 | 0.2–0.4 |
| Emulsifier Stabilizer | .25–2.5 | 0.5–1 |
| Preservative | .05–0.3 | 0.1–0.2 |
| Emulsion Stabilizer | 0.01–2.0 | 0.5–1 |
| SPF Booster | 0.1–5.0 | 0.5–1 |

In order to form the subject composition as water-in-oil emulsions the above ingredients may be dispersed in an emulsified composition by the preparation method discussed below or by any effective method of preparation. As used herein, the term "dispersal" or "dispersed" means that the ingredients are uniformly distributed in the water-in-oil emulsion by any process including dissolving, emulsifying or forming a colloidal suspension, or combinations thereof. Dispersal involves sufficient mixing to eliminate powder or lumps from the composition on visual observation.

The present cosmetic makeup composition is a water based pigmented emulsion containing from about 50 to 75 wt %, preferably from about 52 to about 65 wt % of an oil phase, based on the total weight of the composition. The other 25 to 50 wt % of the present composition is an aqueous phase. The present cosmetic makeup composition can be formulated as a foundation cream, liquid or paste makeup base, preferably as a foundation cream, e.g. an under makeup cream. The cream cosmetic makeup composition of the present invention is generally a water-in-oil emulsion, which provides a very high textured cosmetic product, i.e. a product that feels good when applied to the skin. However, the oil carrier fluid of the present makeup composition may also be a volatile cyclomethicone, or other volatile oil, such as, isododecane, petroleum distillates and isoparaffins.

The various ingredients of the revitalizing makeup composition of this invention are discussed below and are each optimized for use in a water-in-oil emulsion by adjusting the amounts or by coating the ingredients with a surface agent, for example.

ANTI-AGING INGREDIENTS

Sunscreen Agent

The agents for retarding the aging effects of sunlight on the skin are selected from known physical UV blocking sunscreens, including inorganic pigments, such as, for example, titanium dioxide and zinc oxide, or organic UV absorbing sunscreens, such as, for example, p-aminobenzoic acid, cinoxate, diethanolamine p-methoxycinnamate, digalloyl trioleate, dioxybenzone, ethyl 4-[bis[hydroxypropyl] aminobenzoate, 2-ethylhexyl 2-cyano-3,3-diphenylacrylate, ethylhexyl p-methoxycinnamate, 2-ethylhexyl salicylate, glyceryl aminobenzoate, homosalate (3,3,5-trimethylcyclohexylsalicylate), lawsone (2-hydroxy-1,4naphthoquinone) with or without dihydroxyacetone, methyl anthranilate, oxybenzone, Padimate A, Padimate 0, 2-phenylbenzimidazole-5-sulfonic acid, triethanolamine salicylate, red petroleum and sulisobenzone.

Most preferably, ultrafine titanium dioxide coated with an agent, such as, for example, aluminum oxide, to provide light stability thereto is used in the makeup composition. The coated particles may also be surface treated to reduce surface activity and, hence agglomeration. Surface treatment of titanium dioxide or titanium dioxide coated with alumina includes, for example, a silicone surface treatment, preferably a dimethicone treatment using dimethicone oil or a stearic acid surface treatment. Titanium dioxide particles that are treated with both stearic acid and alumina are most preferably used as a sunscreen agent in the present cosmetic compositions. Preferably, the double coated titanium oxide particles have a particle size in the range of from 12 to 20 nanometers (nm), most preferably about 15 to 18 nm. As such, the titanium oxide sunscreen agent of the present composition has a particle size much smaller than that of the titanium dioxide which may be included as pigment, the latter of which has a particle size in the range of from about 45 to 60 nm. Stearic acid and alumina coated ultrafine titanium dioxide particles are commercially available, such as UV-Titan M160 from Presperse, Inc., South Plainfield, N.J. It has been found that alumina coating and stearic acid coating of titanium dioxide particles of a size range of from 12 to 20 nm allows easy incorporation of the sunscreen into a water-in-oil composition without agglomeration of the particles. Because the coated titanium particles used in the present composition do not agglomerate when added to a water-in-oil based composition, a high sun protection factor (SPF) value can be obtained.

In a most preferred embodiment, ultrafine titanium dioxide particles coated with alumina and stearic acid are used in combination with another physical sunscreen, such as, for example, ultrafine zinc oxide particles, preferably stearic acid coated and dimethicone coated zinc oxide particles, such as Z-COTE, available from Sun Smart, Inc. When zinc oxide is used as the sunscreen component of the present cosmetic composition, it is preferred that it be used together with another sunscreen, preferably another physical sunscreen, such as ultrafine titanium dioxide particles, since zinc oxide is recognized by the FDA as a category III sunscreen.

The sunscreen component of the present invention is preferably used at an effective amount to provide a sun protection factor (SPF) of from about 10 to about 15, although the amount of sunscreen component can be varied to provide the desired SPF, generally in the range of from about 4 to about 30. Although the amount of the sunscreen component of the present cosmetic composition will depend, in general, on the desired effect and/or blocking or UV absorbing properties of the sunscreen, it will generally be in the range of from about 0.1 to about 20 wt % of the total composition, preferably in the range of from about 0.5 to 15 wt % and most preferably from about 6 to 10 wt % based on the total weight of the composition.

The sunscreen agent of the present cosmetic makeup composition may also include an agent to boost sunscreen efficacy, such as, for example, shea butter and ELIFAC™ I-205, isoarachidyl neopentanoate emollient available from Bernel Chemical, Co., Englewood, N.J. The SPF booster is incorporated in an amount of from about 0.1 to 5 wt %, preferably about 0.5 to 1 wt %.

Free-Radical Scavenger

Skin cell damage is thought to occur, in part, due to the effect of free radicals, which are highly unstable molecules capable of causing damaging reactions in tissues. Free radicals are produced during biochemical reactions in the body which involve oxygen. Free radicals are normally kept in check by the neutralizing action of naturally occurring antioxidants, such as vitamin E and vitamin C.

Vitamin E and vitamin C are rather unstable in emulsions and therefore, degenerate quickly in such compositions. The present makeup composition contains stabilized free radical scavenger, which is stable in the presence of a water-in-oil emulsion. The free radical scavenger is a compound having anti-oxidant activity that neutralizes free radicals. Such free radical scavengers are selected from stabilized vitamin C compounds including, for example, ascorbyl palmitate and ascorbic acid polypeptide (Vitazyme C, available commercially from Brooks Ind., Inc., South Plainfield, N.J.); stabilized forms of vitamin E compounds, including for example, dl-alpha-tocopherol acetate, protein bonded vitamin E (Tocopherol polypeptide, available from Brooks Ind., Inc., South Plainfield, N.J.); stabilized Beta Carotene compounds, such as Vitazyme A-Plus, a retinol palmitate/carrot protein/beta-carotene complex (Brooks Ind., Inc., South Plainfield, N.J.); and botanical extracts known to contain free radical scavengers, such as for example, ginkgo biloba and combinations thereof. The free radical scavenger is preferably incorporated in an amount of from about 0.1 to about 2 wt %, preferably from about 0.15 to 1 wt % based on total weight of the composition.

To maintain the color of the present makeup composition and prevent malodorous developments, any of the known antioxidants other than those having free radical scavenging activity may also be included in the cosmetic composition in addition to the free radical scavenger component. An example of a suitable antioxidants include TENOX II, obtained from Eastman Chemical Products, Inc., Kingsport, Tenn. However, other known antioxidants, alone or in combination, can be included in the present cosmetic makeup composition, such as, for example, tocopherol acetate, magnesium ascorbyl phosphate, ascorbyl polypeptide, ascorbyl dipalmitate, licorice extract, mulberry extract, green tea extract, L-lysine, lauroylmethionin, superoxide dismutase, BHA, BHT, silymarin, extract of milk-thistle, ladies mantle extract and horsetail extract. The additional and optional antioxidant is incorporated in an amount of from about 0.1 to about 5 wt %, preferably from about 0.25 to 1 wt % based on the total weight of the composition.

Moisturizing Agent/Re-hydrating Ingredients

The cosmetic makeup composition of the present invention contains at least one moisturizing agent/re-hydrating agent and, preferably, a blend of moisturizing and re-hydrating ingredients. For example, the moisturizing agent/re-hydrating agent may be D,L-panthenol, D-panthenol, vitamin A palmitate, vitamin E acetate, methylsilanetriol mannuronate, natural oils such as tallow oil, macadamia nut oil, borage oil, evening primrose oil, kukui nut oil, rice bran oil, tea tree oil, a medium chain fatty acid ester of glycerol, such as glycerol triheptanoate, glyceryl trioctanoate, glycerol trioctanoate, silicones, silicone derivatives and plant extracts containing combinations of botanical compounds such as flavanoids, phenolic compounds, cationic tannins, amino acids, saposids, and mineral salts, for example. Mixtures of two or more of these ingredients may be used. A preferred moisturizing agent/re-hydrating agent is evening primrose oil, which is rich in free fatty acids. An especially preferred combination of moisturizing and re-hydrating agents includes evening primrose oil and botanical extract. Phytelene Complex EGX 244, which is a combination of all of the above listed botanical components can be used in the present composition. Other moisturizing agents/re-hydrating agents may also be incorporated in the form of phospholipid encapsulated vesicles, such as, for example, phospholipid encapsulated Vitamin E and phospholipid encapsulated mineral water.

Preferably, the total amount of moisturizing agent/re-hydrating agent component of the present makeup composition is in the range of from about 0.5 to about 13 wt % based on the total weight of the composition, and most preferably is in the range of from about 1 to 10 wt % of the total composition.

Skin Firming Agent

The makeup composition of the present invention also contains as an essential ingredient, a skin firming agent, preferably an animal derived ceramide cosmetic ingredient, although ceramides from plant sources or other sources may also be used. It is well known in the field of cosmetics that ceramides, which are lipids present in the intercellular lipid layers of the outer layers of the skin, such as glycoceramides play an important role in maintaining the water permeability barrier of the skin and hence, the firmness of the skin. The skin firming agent of the present composition functions by retaining fluids in the skin and assisting in the transport of ions, fatty acids, lipids and other essential nutrients at the cellular level. The effect is a firming effect on the skin.

The present skin makeup composition contains a skin firming effective amount of at least one glycolipid, preferably a naturally occurring glycolipid derived from animal tissue to help maintain the integrity of the barrier function of the skin. Preferably, combinations of animal-derived sphingolipids, phospholipids, ceramides, and glycoceramides are added to the present composition. Alternatively, ceramides from plant sources or hydrolyzed proteins from various sources can be added to the present makeup composition. An example of an animal-derived mixture of glycoceramides is Glyco/Cer, available commercially from Intergen Co., Purchase, N.Y.

Generally, a mixture of glycoceramides is added in an amount of from about 0.0001% to 0.1%, preferably from about 0.01% to 0.05%, based on total weight of the composition.

Colorant/Pigment

The present cosmetic makeup composition also contains cosmetically acceptable inorganic pigment or pigments or colorants, such as, for example titanium dioxide having a particle size larger than the ultra fine titanium oxide used as a sunscreen agent (e.g. about 45 to 60 nm), yellow pure oxy, black pure oxy, pink lomicron, russet iron oxide, talc, red iron oxide, D & C Red #30 Lake, FD&C Yellow #6 Aluminum Lake and combinations thereof. The combination of pigments and amount of pigment or colorant incorporated into the present composition depends upon the particular color desired, however, in general an amount of pigment or colorant in the range of from about 0.5 to 20 wt %, preferably, 5 to 15%, is used.

Because the present composition is a water-in-oil based emulsion, it is preferred that the pigment particles are coated with an agent, such as dimethicone to provide an outer hydrophobic coat. Dimethicone coating of the pigment particles also provides an improved wear characteristic to the composition. However, non-coated pigments may also be used, alone or in combination with coated pigments. Pigments such as titanium oxide and iron oxides can be coated with a variety of materials. Preferably, the coated pigments used in the present invention are coated with dimethicone, however, other coatings, such as, for example, methicone, lecithin, amino acids, metal salts, collagen, polyacrylates, polyethylene, fluorosilicone, perfluoroalkyl phosphate or isopropyl titanium triisosterate may be absorbed to the pigment particles.

OPTIONAL INGREDIENTS

Preservative

The cosmetic makeup composition is manufactured under clean but non-sterile conditions, therefore preservatives are used to prevent growth of microorganisms. A sufficient quantity of one or more preservatives is added to the makeup composition so that the emulsified cosmetic makeup composition withstands bacterial growth from an experimental inoculation for at least three months.

The cosmetic makeup composition can be prepared with, for example, natural antimicrobial agents, such as tea tree oil and cedar oil, or organic preservatives such as, propylene glycol, trisodium EDTA, methylparaben, propylparaben, ethylparaben, butylparaben, phenoxy ethanol, hexamidine isothionate, commercially prepared products such as GERMALL™ II and GLYDANT™, for example, and combinations thereof. The amount of preservative incorporated into the present composition is generally in the range of from about 0.1 to about 1.5 wt %, preferably, from about 0.25 to 0.75 wt % based on the total weight of the composition.

Propylene glycol can be added in amounts sufficient so as to serve as both a humectant and preservative of the cosmetic composition, such as from about 0.5 to 15.0 wt %, preferably from about 1 to 5 wt % based on the total weight of the composition.

Emollients, Anti-Irritating, Anti-Inflammatory, and/or Healing Agents

The present cosmetic makeup composition may also contain an amount of emollient to provide a soothing and softening effect to the skin and can include at least one anti-irritant agent, anti-inflammatory agent, healing agent or combination thereof. Many emollients also have anti-inflammatory, healing or anti-irritating properties or combinations thereof. The emollient ingredients may be added to the cosmetic makeup composition in an amount of from about 0.5 to about 25 wt %, preferably about 5 to about 15 wt % of the total weight of the composition. Examples of calming, soothing and softening agents which may be included in the present cosmetic makeup composition include Vitamin A palmitate; Phytelene Complex EGX 244, which is a botanical blend of extracts of calendula, chamomile, linden, cornflower, matricaria and hypericum; allantoin; dipotassium glycyrrhizinate; stearyl glycyrrhizinate; bisabolo((3-cyclohexene-1-methanol-$\propto$,4-dimethyl-$\propto$(4-methyl-3-pentenyl)); squalane NF; cetyl ester wax; shea butter; orange roughy oil; hydrogenated phospholipids, and HETESTER™ FAO, which is a $C_{12}$–$C_{15}$ alcohol octanoate, available from Bernel Chemical Company, Englewood, N.J. Suitable emollients can be employed if desired. Those emollients include the following classes, for example:

1. hydrocarbon oils and waxes, such as mineral oil, polyethylene and paraffin;
2. triglyceride esters, such as olive oil, avocado oil, and squalene;
3. lanolin and derivatives;
4. ether-esters, such as fatty acid esters of ethoxylated fatty alcohols; and
5. fatty acids having 10 to 20 carbon atoms, such as lauric, myristic, oleyl, and stearate.

In addition to the emollient component, an anti-irritant, anti-inflammatory and/or healing agent may be added to the present makeup composition. Particularly preferred anti-irritants and anti-inflammatory agents that may be incorporated into the present cosmetic composition include dipotassium glycyrrhizic acid, stearyl glycyrrhizic acid and bisabolol. Glycyrrhizic acid is a glycyrrhetinic acid glycoside which may be obtained from natural licorice plant extracts. The anti-irritant/anti-inflammatory component is incorporated into the present composition in an amount of from about 0.5 to about 5 wt %.

Emulsifier

At least one emulsifier may be combined with water, preferably demineralized water, to form the emulsified base of the present cosmetic makeup composition. The emulsifier forms a stable bridge between the water and water-soluble ingredients and the oily or water insoluble ingredients of the composition. Preferably, a nonionic emulsifier, such as cetyl dimethicone copolyol or dimethicone polyol is used in the present cosmetic makeup composition, either alone or in combination with other emulsifiers, preferably other nonionic emulsifiers.

The amount of emulsifier incorporated in the present composition is in the range of about 0.5 to about 6 wt %, preferably, about 2 to about 3.5 wt %.

Other suitable emulsifiers, preferably nonionic emulsifiers, may be used and include, for example, sorbitan esters and its ethoxylates, methyl sucrose esters and its ethoxylates, fatty alcohol ethoxylates, wherein the fatty acid moiety contains less than 20 carbon atoms; and block copolymers of propylene oxide and ethylene oxide. Typical of the useful commercially available emulsifiers, mention can be made of ABIL-90 (a cetyl dimethicone copolyol), Amphisol™, Lipo GMS 450, Solulan C-24, glucamate SSE 20 and glucate SS.

Other Optional Adjuvants

Various other cosmetically acceptable ingredients can be included in the cosmetic makeup composition of the present invention, including, for example, fragrance, defoamers, such as a silicone or silicone derivative material, pH buffers, such as triethanolamine, bodying agents, such as stearic acid and cetyl alcohol, light reflectants, fillers, such as talc, wax to provide a cushioning effect, and polymer based deposition and delivery compounds such as POLYOLPREPOLYMER 2™ available from Barnet, Ind., Inc., Englewood Cliffs, N.J. Other optional ingredients include, for example, emulsion stabilizer, such as, sodium chloride, potassium chloride, ammonium chloride or any other monovalent salt of a strong acid or strong base; sorbitol; sodium PCA; and glycerin. These optional ingredients can be added alone or in combination and when used are added in cosmetically effective amounts. Approximate ranges of amount of each of these optional ingredients are listed in Table 1.

PREPARATION OF COSMETIC MAKEUP COMPOSITION

The cosmetic makeup composition of the invention can be formulated as a foundation cream, liquid or paste makeup base, which differ primarily in viscosity whereby beneficial effects are produced by application of the makeup composition to the skin.

The cosmetic makeup composition of the invention can be prepared by a batch operation or by in-line blending techniques.

Example
Composition of a Cream Natural Defense Makeup
A. Formulation

Part 1

| | |
|---|---|
| 34.315% | Water |
| 23.5% | Cyclomethicone |
| 0.5% | ISOLAN ™ GI-34 |
| 0.1% | evening primrose oil |
| 2.0% | shea butter |
| 4.0% | ELEFAC ™ I-205 |
| 2.5% | ABIL ™ EM-90 |
| 0.5% | Tocopherol Acetate |
| 0.1% | Retinyl Palmitate |
| 1.0% | ABILWAX ™ 9814 |
| 1.5% | TRIVENT ™ PE-48 |
| 0.2% | Propylparaben |
| 0.025% | Glyco/ceramide mixture |
| 20.15% | Pigment/sunscreen mixture C |
| 0.5% | sodium chloride |
| 0.25% | Ginkgo biloba |
| 1.0% | Dipropylene glycol |
| 1.0% | Panthenol-D |
| 1.0% | Phytelene Complex EGX 244 |
| 0.1% | Vitazyme C |
| 0.2% | Dipotassium glycyrrhizinate |
| 0.01% | Sodium hyaluronate |
| 0.2% | Germall ™ II |
| 5.0% | Butylene glycol |
| 0.15% | Methyl paraben |
| 0.2% | Fragrance AN 101651 |

PIGMENT/SUNSCREEN MIXTURE C

| | |
|---|---|
| 26.05% | Titanium dioxide and dimethicone (SAT-T-47051) |
| 4.12% | Yellow iron oxide C33-U073 UL SIL |
| 0.97% | Red iron oxide C33-U075 UL SIL |
| 0.70% | Black iron oxide C33-U198 UL SIL |
| 17.29% | Talc J-68-SAT |
| 1.24% | Silica silylate |
| 44.67% | UV-Titan M160 |
| 4.96% | Z-cote |

The above cream cosmetic makeup composition is prepared as follows.

Referring to Table 2, the makeup composition is prepared by forming a first mixture by combining the ingredients of mixture A (Table 2) at room temperature and then heating the ingredients to 50° to 55° C. until a uniform dispersion is obtained, at which time the single component of mixture B (Table 2) is added and mixed until smooth, e.g., about 10 minutes. The temperature is adjusted to about 30° to 35° C. The components of mixture C (color mix; Table 2) are then added and mixed until a uniform blend is obtained. The color mix is formed by a two-step process described below and then added with mixing to the composition and the batch color phase is tested for color quality. When the color quality of the color phase mixture is satisfactory, the mixture is transferred to a steam jacketed kettle equipped with double motion agitation. The cyclomethicone (Mixture D) is used to rinse the color phase kettle and is then added to the steam jacketed kettle.

Mixture E (water phase) is formed separately at 30° to 35° C. and mixed until uniform.

Mixture F is also formed separately, under agitation and heated to 55° until a clear solution results. Mixture F is then added to Mixture E (water phase) and mixed for about 15 minutes.

The mixture of the water phase (Mixture E) plus Mixture F is then added to the color phase (Mixtures A, B, C and D) at a rate that prevents layering of the water on top of the color phase. After the water phase addition is complete, the mixture is maintained at 30° to 35° C. under agitation until a homogenous mixture is obtained.

Fragrance (Mixture G) is added to the above mixture under agitation at 30° to 35° C. The mixture is then homogenized until the desired viscosity is obtained.

Mixture C (color mix) is obtained by milling the colorants to disperse the various pigments uniformly (part 1) and separately mixing the sunscreen agents (part 2). The sunscreen agents (part 2) are added to the colorants (part 1) and mixed for about 20 to 30 minutes until a uniform mixture is obtained.

Although the present invention has been described with reference to a preferred embodiment thereof, other versions of the cosmetic makeup composition are possible. Therefore, the spirit and scope of the appended claims should not be limited to the preferred version contained herein.

The cosmetic makeup composition of the present invention is topically applied in a conventional manner, as by dispersing from a container as needed. The composition is easily spread on the skin surface and leaves the skin with a soft and smooth appearance. The makeup composition of the present invention is formulated to exert the following desirable effects: (1) anti-aging effects, (2) moisturizing and hydrating effects, (3) firming and elasticity effects, (4) anti-wrinkle effects and (5) complexion improvement.

TABLE 2

Method of Preparation of Natural Defense Makeup Composition

| Ingredient | Concentration % by weight of total composition |
|---|---|
| Mixture A | |
| Cetyl dimethicone copolyol (emulsifier) | 2.5 |
| Vitamin E acetate (anti-oxidant) | 0.5 |
| Vitamin A palmitate (moisturizer) | 0.1 |
| Cetyl dimethicone (emollient) | 1.0 |
| Pentaerythritol tetraoctanoate (emollient) | 1.5 |
| Polyglycerol-4 isosterate (emulsifier) | 0.5 |
| Evening primrose oil (moisturizer) | 0.1 |
| Shea butter (SPF booster, emollient) | 2.0 |
| Octyldodecyl neopentanoate (Elefac ™ I205) (SPF booster, emollient) | 4.0 |
| Propylparaben (preservative) | 0.2 |
| Glyco/ceramide Complex (skin firming agent) | 0.025 |
| Mixture B | |
| Cyclomethicone (carrier fluid, volatile silicone) | 21.5 |

TABLE 2-continued

Method of Preparation of Natural Defense Makeup Composition

| Ingredient | |
| --- | --- |
| Mixture C | |
| COLOR MIX (pigments) | 20.15 |
| Mixture D | |
| Cyclomethicone (carrier fluid, volatile silicone) | 2.0 |
| Mixture E | |
| Water | 34.315 |
| Sodium chloride (emulsion stabilizer) | 0.5 |
| Ginkgo biloba (free radical scavenger/anti-oxidant) | 0.25 |
| Dipropylene glycol (humectant) | 1.0 |
| Panthenol (moisturizer) | 1.0 |
| Phytotene complex EGX 244 (moisturizer, anti-irritant) | 1.0 |
| Vitazyme C (free radical scavenger) | 1.0 |
| Dipotassium glycerrhizinate (anti-irritant) | 0.2 |
| Sodium hyaluronate (humectant) | 0.01 |
| Germall ™ II (Preservative) | 0.2 |
| Mixture F | |
| Butylene glycol (humectant) | 5.0 |
| Methylparaben (preservative) | 0.15 |
| Mixture G | |
| Fragrance | 0.2 |
| Mixture C - Color Mix | wt % of total |
| Part 1 - Pigment | of Mixture C |
| SAT Titanium dioxide | 26.05 |
| Yellow iron oxide | 4.12 |
| Red iron oxide | 0.97 |
| Black iron oxide | 0.7 |
| Talc and dimethicone | 17.29 |
| Silica silyate | 1.24 |
| Part 2 - Sunscreen | |
| Titantium dioxide-stearic acid and Alumina treated (UV-Titan MIGO) | 44.67 |
| Zinc oxide-stearic acid alumina treated (Z-cote) | 4.96 |

What is claimed is:

1. An emulsified cosmetic makeup composition for smoothing, moisturizing, firming and protecting human skin from the effects of the enviroment and improving the complexion of the skin comprising a water-in-oil emulsion and emulsified and dispersed therein in cosmetically effective amounts (a) sunscreen agent;

(b) free radical scavenger;

(c) moisturizing agent/re-hydrating agent;

(d) skin firming agent; and (e) cosmetically acceptable pigment.

2. The makeup composition of claim 1 wherein the skin firming agent comprises a mixture of animal and/or botanical ceramides and glycolipids.

3. The makeup composition of claim 1 wherein the sunscreen agent comprises ultrafine particles of titanium dioxide coated with aluminum oxide and stearic acid.

4. The makeup composition of claim 3 wherein the sunscreen agent (a) is present in an amount sufficient to provide a sun protection factor of at least about 10.

5. The makeup composition of claim 1 wherein the free radical scavenger (b) is selected from the group consisting of a stabilized vitamin E compound, stabilized vitamin C compound, ginkgo biloba extract and combinations thereof.

6. The makeup composition of claim 1 wherein the moisturizing agent/re-hydrating agent (c) comprises evening primrose oil, shea butter, octyldodecyl neopentanoate, panthenol, sodium hyaluronate, cetyl dimethicone, pentaerythritol tetraoctanoate and a moisturizing botanical extract.

7. The makeup composition of claim 1 wherein the cosmetically acceptable pigment (e) comprises dimethicone-coated pigment particles.

8. The makeup composition of claim 1 further comprising emollient.

9. The makeup composition of claim 1 further comprising emulsifier.

10. The makeup composition of claim 1 wherein the pigment (e) is present in an amount of from about 0.5 to 2.5 wt % based on the total weight of the composition.

11. An emulsified cosmetic makeup composition for smoothing, moisturizing, firming and protecting human skin from the effects of sunlight and improving the complexion of the skin comprising in a water-in-oil emulsified base, based on the total weight of the composition, from about 0.1 to 20 wt % stearic acid and aluminum oxide coated ultrafine titanium dioxide particles as sunscreen agent; from about 0.1 to 2% free-radical scavenger; from about 0.5 to 13% of a blend of moisturizers and re-hydrating agents comprising evening primrose oil and a moisturizing botanical extract; from about 0.0001 to 0.1% of a mixture of animal and/or botanical ceramides and glycolipids; and from about 0.5 to 25% of a blend of cosmetically acceptable pigments comprising dimethicone-coated pigments.

12. The cosmetic makeup composition of claim 11 further comprising an amount of from 0.5 to 25% of emollient, anti-irritant agent, healing agent, anti-inflammatory agent or combination thereof, based on the total weight of the composition.

13. The cosmetic composition of claim 11 further comprising an amount of from 0.5 to 6% of emulsifier comprising cetyl dimethicone copolyol or dimethicone polyol, based on the total weight of the composition.

14. An emulsified cosmetic makeup composition of claim 12 comprising from about 6 to about 10% stearic acid and aluminum oxide coated ultrafine titanium dioxide particles as sunscreen agent; from about 0.15 to about 1% ginkgo biloba as free radical scavenger; from about 1 to about 10% of a blend of moisturizers and re-hydrating agents comprising evening primrose oil, shea butter, octyldodecyl neopentanoate, panthenol, sodium hyaluronate, cetyl dimethicone, pentaerythritol tetraoctanoate and a moisturizing botanical blend of extracts of canendula, chamomile, linden, cornflower, matricaria and hypericum; from about 0.01 to about 0.05% of a complex of animal ceramides and glycolipids as skin firming agent; from about 5 to about 15% of a blend of cosmetically acceptable pigments comprising dimethicone-coated pigments; and from about 0.15 to about 0.35% fragrance.

15. A method of smoothing, firming, moisturizing and protecting from sunlight and improving the complexion of human skin comprising topically applying to the skin a cosmetically effective amount of water-in-oil emulsified makeup composition comprising cosmetically effective amounts of skin tightening agent comprising ceramides and glycolipids; sunscreen agent; moisturizing agent/rehydrating agent; cosmetically acceptable pigment and free-radical scavenger.

16. The method of claim 15 wherein the sunscreen agent comprises stearic acid and aluminum oxide coated ultrafine titanium oxide particles; the moisturizing agent/re-hydrating agent comprises a blend of evening primrose oil and a moisturizing botanical extract; and the free-radical scavenger comprises stabilized vitamin C, stabilized vitamin E, extract of ginkgo biloba or a combination thereof.

* * * * *